(12) United States Patent
Tearney et al.

(10) Patent No.: US 10,845,546 B2
(45) Date of Patent: Nov. 24, 2020

(54) SYSTEMS AND METHODS FOR PROVIDING AN OPTICAL ROTARY JOINT

(71) Applicant: The General Hospital Corporation, Boston, MA (US)

(72) Inventors: Guillermo J. Tearney, Cambridge, MA (US); Zhonglie Piao, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 16/480,947

(22) PCT Filed: Jan. 29, 2018

(86) PCT No.: PCT/US2018/015735
§ 371 (c)(1),
(2) Date: Jul. 25, 2019

(87) PCT Pub. No.: WO2018/140875
PCT Pub. Date: Aug. 2, 2018

(65) Prior Publication Data
US 2019/0391338 A1    Dec. 26, 2019

Related U.S. Application Data

(60) Provisional application No. 62/451,511, filed on Jan. 27, 2017.

(51) Int. Cl.
*G02B 6/26* (2006.01)
*G02B 6/36* (2006.01)
(Continued)

(52) U.S. Cl.
CPC ........ *G02B 6/3604* (2013.01); *A61B 1/00128* (2013.01); *A61B 1/07* (2013.01); *A61B 5/0066* (2013.01)

(58) Field of Classification Search
CPC ................ G02B 6/3604; G02B 6/3825; A61B 1/00128; A61B 1/07; A61B 5/0066
See application file for complete search history.

(56) References Cited

U.S. PATENT DOCUMENTS 4,989,946 A * 2/1991 Williams ............. G02B 6/3504
                                                        385/16
6,898,346 B2    5/2005 Mercey
(Continued)

FOREIGN PATENT DOCUMENTS

FR    2527790 A1    12/1983
GB    2185590 A     7/1987

OTHER PUBLICATIONS

Fard, A. M., et al. "Optical coherence tomography—near infrared spectroscopy system and catheter for intravascular imaging." Optics express 21.25 (2013): 30849-30858.
(Continued)

*Primary Examiner* — Ellen E Kim
(74) *Attorney, Agent, or Firm* — Quarles & Brady LLP

(57) ABSTRACT

Systems for providing an optical rotary joint are provided. In some embodiments, a system comprises: a lens-less optical rotary joint, comprising: a guide ferrule; a rotatable ferrule; a rotatable optical fiber, the rotatable optical fiber passing through the rotatable ferrule and the guide ferrule, the rotatable optical fiber being secured within the rotatable ferrule, and the rotatable optical fiber being freely rotatable within the guide ferrule; and a coupler to secure the guide ferrule and receive a static ferrule including a static optical fiber such that a face of the static optical fiber is proximate a face of the rotatable optical fiber.

16 Claims, 10 Drawing Sheets

(51) Int. Cl.
  *A61B 1/00* (2006.01)
  *A61B 1/07* (2006.01)
  *A61B 5/00* (2006.01)

(56) References Cited

U.S. PATENT DOCUMENTS

| | | | |
|---|---|---|---|
| 7,382,949 B2 | 6/2008 | Bouma | |
| 8,355,607 B2 | 1/2013 | Zhang | |
| 8,909,008 B1 | 12/2014 | Tzeng | |
| 8,965,151 B1 | 2/2015 | Zhang | |
| 9,429,713 B2 * | 8/2016 | Thornton, Jr. | A61B 90/70 |
| 2006/0013537 A1 * | 1/2006 | Miyake | G02B 6/3833 |
| | | | 385/60 |
| 2006/0093276 A1 | 5/2006 | Bouma | |
| 2010/0054670 A1 * | 3/2010 | Milette | G02B 6/3846 |
| | | | 385/83 |
| 2012/0069348 A1 | 3/2012 | Jono | |
| 2013/0163930 A1 * | 6/2013 | Jian | G02B 6/3882 |
| | | | 385/60 |
| 2014/0142436 A1 * | 5/2014 | Hutchins | A61B 5/0035 |
| | | | 600/478 |

OTHER PUBLICATIONS

Gora, M. J., et al. "Tethered capsule endomicroscopy enables less invasive imaging of gastrointestinal tract microstructure." Nature medicine 19.2 (2013): 238.
Hariri, L. P., et al. "Toward the guidance of transbronchial biopsy: identifying pulmonary nodules with optical coherence tomography." Chest 144.4 (2013): 1261-1268.
International Searching Authority, International Search Report and written opinion for application PCT/US2018/015735, dated May 10, 2018, 13 pages.
Suter, M. J., et al. "Esophageal-guided biopsy with volumetric laser endomicroscopy and laser cautery marking: a pilot clinical study." Gastrointestinal endoscopy 79.6 (2014): 886-896.
Tearney, G. J., et al. "Three-dimensional coronary artery microscopy by intracoronary optical frequency domain imaging." JACC: Cardiovascular imaging 1.6 (2008): 752-761.
Yoo, H., et al. "Intra-arterial catheter for simultaneous microstructural and molecular imaging in vivo." Nature medicine 17.12 (2011): 1680.
Yun, S. H., et al. "Comprehensive volumetric optical microscopy in vivo." Nature medicine 12.12 (2006): 1429.
European Patent Office. Extended European Search Report for application 18744914.5. dated Sep. 15, 2020.

\* cited by examiner

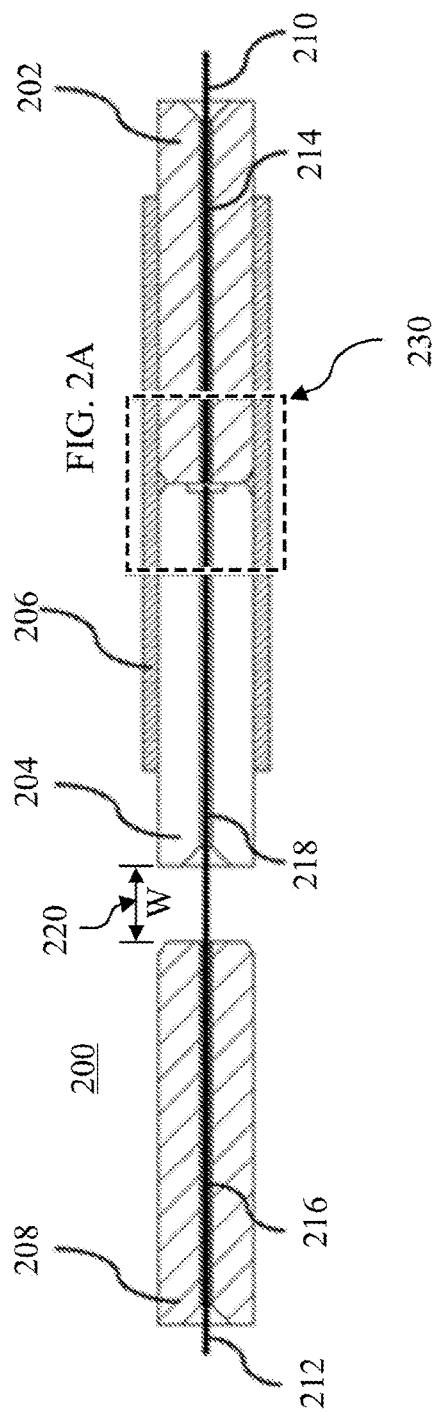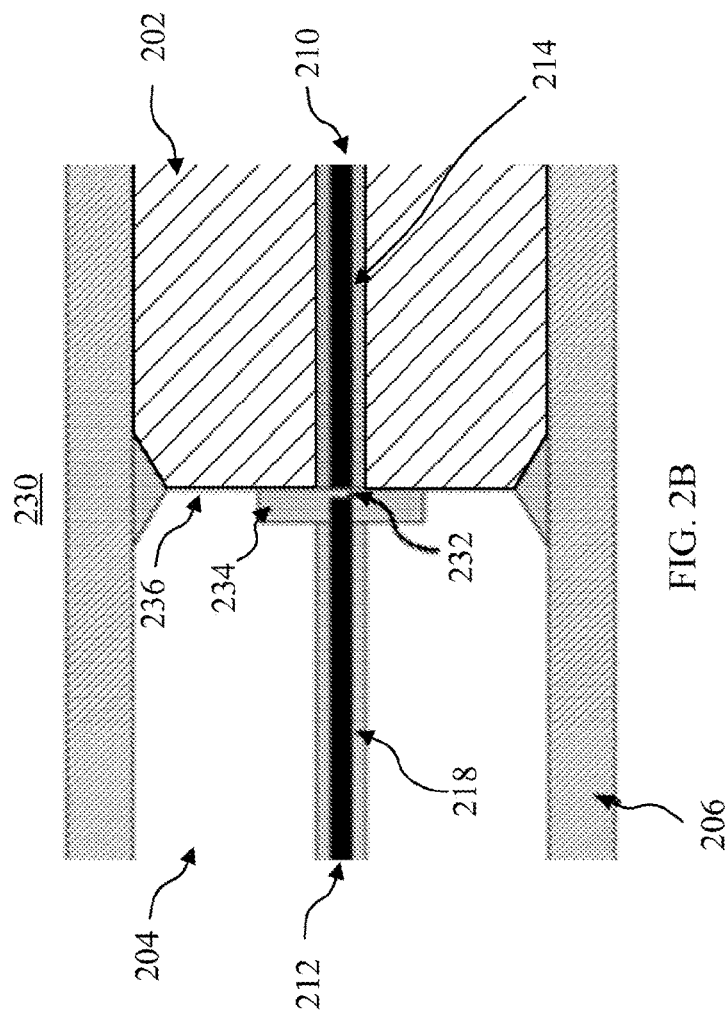

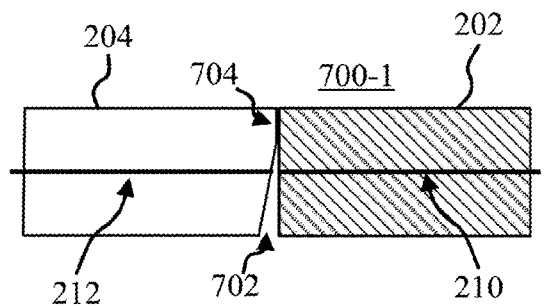
FIG. 7A1
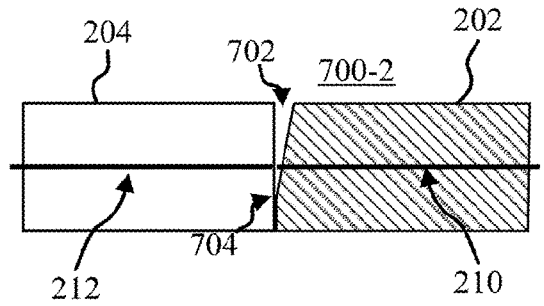
FIG. 7A2
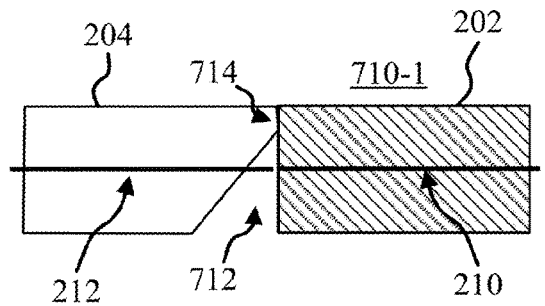
FIG. 7B1
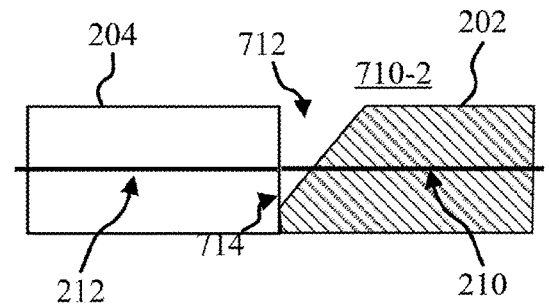
FIG. 7B2
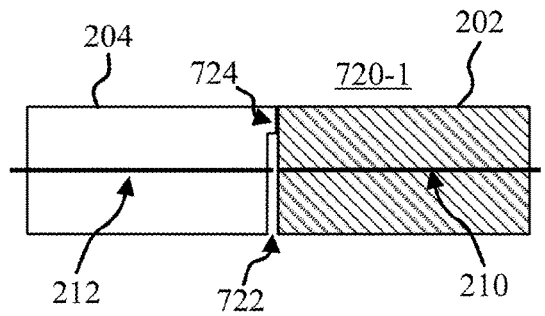
FIG. 7C1
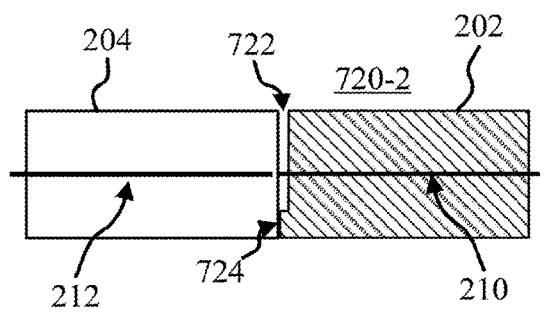
FIG. 7C2

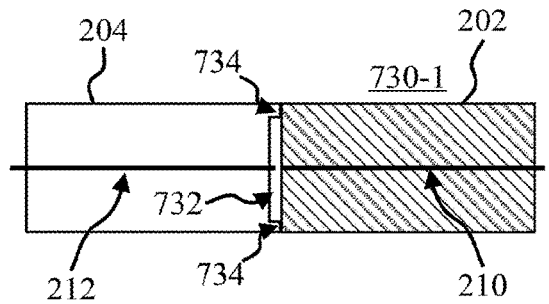
FIG. 7D1
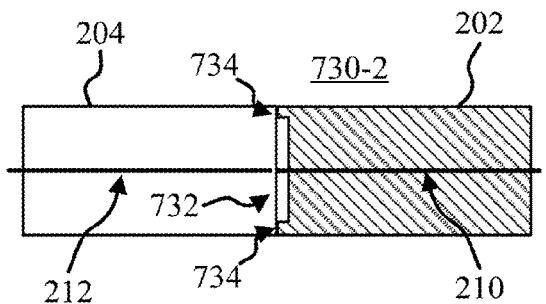
FIG. 7D2
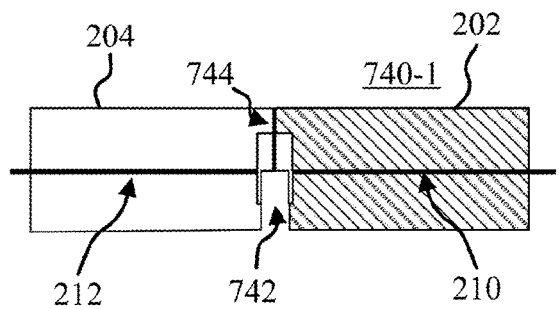
FIG. 7E1
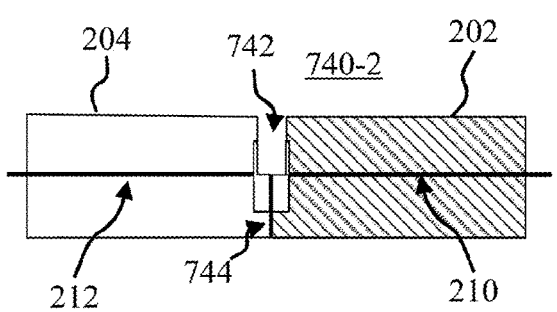
FIG. 7E2
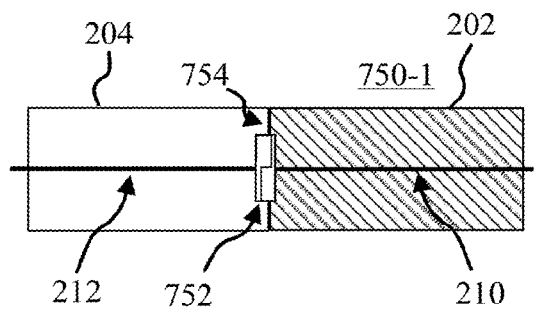
FIG. 7F1
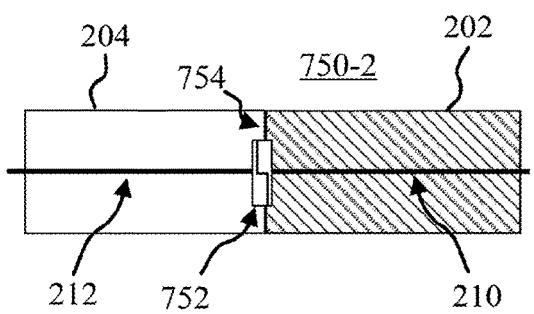
FIG. 7F2

SYSTEMS AND METHODS FOR PROVIDING AN OPTICAL ROTARY JOINT

CROSS-REFERENCE TO RELATED APPLICATIONS

This application is a U.S. National Phase of PCT Application No. PCT/US2018/015735 filed on Jan. 29, 2018, which is based on, and claims the benefit of U.S. Provisional Patent Application No. 62/451,511, filed Jan. 27, 2017, which is hereby incorporated herein by reference in its entirety for all purposes.

STATEMENT REGARDING FEDERALLY SPONSORED RESEARCH

N/A

BACKGROUND

Optical fiber rotary joints (sometimes referred to as an optical fiber rotary junction) are widely used in endoscopic/intravascular imaging for transmitting optical power and/or signals between a scanning imaging probe (e.g., a catheter, an endoscope, or a needle) that utilizes rotating optics, and a static imaging device. For example, endoscopic optical imaging techniques (e.g., Optical Coherence Tomography, spectroscopy, Raman spectroscopy, fluorescence imaging, and photoacoustic) have been proposed for use in the diagnosis of broadly diffuse diseases such as coronary artery diseases, gastro intestinal cancer diagnosis, and pulmonary disease.

Many different designs have been proposed for implementing an optical fiber rotary joint, which include diverse types of optics, mechanics, and optical fibers. Such optical fiber rotary joints are designed to rotate or spin one optical fiber with respect to another, while providing a consistent optical connection between the two fibers during rotation.

However, it is difficult to achieve elevated rotational speeds (e.g., on the order of several thousand revolutions per minute). While optical-lens-based rotary joints have been proposed, these designs are typically limited due to the simplicity of the lenses that are typically required (e.g., grin lenses or aspheric lenses), making this type of rotary joint unsuitable for use in combination with complex optical fibers, such as double-clad fibers (DCF) and multi-clad fibers (MCF). For example, to achieve optimal optical transmission (and optimal image quality) using complex optical fibers such as DCF and MCF fibers, it is important to optimize core-to-core and cladding-to-cladding optical coupling for the different wavelengths that may be conducted through the rotary joint to transfer light from the facet of one fiber to the other with less loss. Current lens-based rotary joints are not capable of close core-to-core and cladding-to-cladding optical coupling due to the difficulty of focusing the light with multiple wavelengths at both the center and the periphery of the lens.

Accordingly, new systems for providing an optical rotary joint are desirable.

SUMMARY

In accordance with some embodiments of the disclosed subject matter, systems for providing an optical rotary joint are provided.

In accordance with some embodiments of the disclosed subject matter, a lens-less optical rotary joint is provided, the lens-less optical rotary joint comprising: a guide ferrule; a rotatable ferrule; a rotatable optical fiber, the rotatable optical fiber passing through the rotatable ferrule and the guide ferrule, the rotatable optical fiber being secured within the rotatable ferrule, and the rotatable optical fiber being freely rotatable within the guide ferrule; and a coupler to secure the guide ferrule and receive a static ferrule including a static optical fiber such that a face of the static optical fiber is proximate a face of the rotatable optical fiber.

In some embodiments, the lens-less optical rotary joint further comprises a gap between the face of the static optical fiber and the face of the rotatable optical fiber.

In some embodiments, the gap between the face of the static optical fiber and the face of the rotatable optical fiber has a width of less than 50 μm.

In some embodiments, the guide ferrule comprises an end which mates with the static ferrule, wherein the end of the guide ferrule comprises a reference face which determines the width of the gap.

In some embodiments, the reference face has an area that is less than a cross-sectional area of the static ferrule.

In some embodiments, the rotatable optical fiber is a multi-mode optical fiber, and the lens-less optical rotary joint is compatible with multi-mode optical fibers and single mode optical fibers.

In some embodiments, the lens-less optical rotary joint further comprises a rotatable shaft at least partially enclosing the rotatable ferrule such that rotation of the rotatable shaft around a central axis defined by the rotatable optical fiber causes rotation of the rotatable ferrule around the central axis.

In some embodiments, the lens-less optical rotary joint further comprises: an optical coherence tomography probe comprising rotatable optics, wherein the optical coherence tomography probe is coupled to the rotatable optical fiber; and a static imaging device, wherein the static imaging device is coupled to the static optical fiber, wherein a plurality of continuous optical connections are formed between the static imaging device and the optical coherence tomography probe during rotation of the rotatable optics.

In some embodiments, the rotatable ferrule and the guide ferrule are separated by a spacing.

In some embodiments, the gap has a transmission fluid disposed therein.

In some embodiments, the transmission fluid comprises an index matching gel.

In accordance with some embodiments of the disclosed subject matter, a rotary joint is provided, the rotary joint comprising: a first ferrule comprising an elongate body extending from a first end to a second end, a first through-hole passing between the first end to the second end; a second ferrule comprising an elongate body extending from a third end to a fourth end, a second through-hole passing between the third end to the fourth end; a first optical fiber passing through the second through-hole and the first through-hole, the first optical fiber being secured within the first through-hole, and the first optical fiber being freely rotatable within the second through-hole; a guide to receive the first ferrule and a third ferrule, the third ferrule having a second optical fiber passing therethrough, the guide coaxially aligning the second optical fiber with the first optical fiber to form an optical connection between the second optical fiber and the first optical fiber upon insertion of the third ferrule into the guide; and a rotary shaft coupled to the second ferrule, the rotary shaft being rotatable about an axis defined by the first optical fiber, rotation of the rotary shaft about the axis causing the second ferrule and the first optical fiber to rotate within the first ferrule.

In some embodiments, the rotary joint further comprises an adapter configured to receive the third ferrule, wherein the adapter comprises a connector positioning system configured to align a fiber optic cable connector with the guide, wherein the fiber optic cable connector comprises the third ferrule.

In some embodiments, the rotary joint further comprises: a static connector configured to couple to the fiber optic cable connector; and a rotatable connector configured to couple to an imaging apparatus, the imaging apparatus having rotatable optics.

In some embodiments, the rotary shaft and the rotatable connector are coupled, wherein the rotatable connector causes the rotatable optics to rotate at the same speed as the rotary shaft.

In some embodiments, the rotary joint further comprises a motor coupled to the rotary shaft, wherein rotation of the motor causes rotation of the second ferrule.

In some embodiments, the rotary joint further comprises a gap between the first optical fiber and the second optical fiber, wherein the gap comprises a transmission fluid.

In some embodiments, the gap is less than 50 μm.

In some embodiments, the rotary joint further comprises a buffer space between an outer diameter of the first optical fiber and an inner diameter of the second through-hole, the buffer space being filled with a transmission fluid.

In some embodiments, the transmission fluid comprises an index matching gel.

In some embodiments, the first optical fiber is a double clad fiber.

In some embodiments, the rotary joint further comprises at least one bearing adjacent the rotary shaft.

In some embodiments, the rotary joint further comprises a housing at least partially enclosing and axially aligning the first ferrule, the second ferrule, the guide, and the rotary shaft, wherein the housing comprises: a first component at least partially enclosing the second ferrule and the rotary shaft, and a second component at least partially enclosing the first ferrule and the guide, wherein the position of the second component with respect to the first component is adjustable to axially align the first ferrule and the second ferrule.

In accordance with some embodiments of the disclosed subject matter, a method for transmitting optical signals from a static imaging device to an imaging probe having rotatable optics using a rotary joint is provided, the rotary joint comprising: a first ferrule comprising an elongate body extending from a first end to a second end, wherein a first through-hole passes between the first end to the second end; a second ferrule comprising an elongate body extending from a third end to a fourth end, wherein a second through-hole passes between the third end to the fourth end; a first optical fiber that passes through the second through-hole and passes through at least a portion of the first through-hole, wherein the first optical fiber is secured within the first through-hole and is free to rotate within the second through-hole; a guide that is configured to receive the first ferrule and coaxially align a second optical fiber that passes through at least a portion of a third ferrule with the first optical fiber to form a first optical connection between the first optical fiber and the second optical fiber upon insertion of the third ferrule into the guide; and a rotary shaft coupled to the second ferrule and configured to be rotated about an axis defined by the first optical fiber, wherein rotation of the rotary shaft about the axis causes the second ferrule and the first optical fiber to rotate within the first ferrule; the method comprising: connecting the second optical fiber to the rotary joint by inserting the third ferrule through a static optical connector receptacle to form the first optical connection; connecting the rotatable optics of the imaging probe to the first optical fiber by inserting at least a portion of the rotatable optics into a rotatable optical connector receptacle; rotating the first optical fiber and the rotatable optics using a motor; receiving a first optical signal from the static imaging device; transmitting the first optical signal from the static imaging device to the rotatable optics through the first optical connection and the second optical connection during rotation of the first optical fiber; receiving a second optical signal from the imaging probe; and transmitting the second optical signal from the imaging probe to the static imaging device through the first optical connection and the second optical connection during rotation of the first optical fiber.

In some embodiments, the rotary joint further comprises a gap between the first optical fiber and the second optical fiber.

In some embodiments, the gap has an index matching gel disposed therein.

In some embodiments, the gap has a width of less than 50 μm.

In some embodiments, the first ferrule and the second ferrule are separated by a spacing.

In accordance with some embodiments of the disclosed subject matter, a method for transmitting optical signals from a static imaging device to an imaging probe with rotatable optics using a lens-less optical rotary joint is provided, wherein the lens-less optical rotary joint comprises: a guide ferrule; a rotatable ferrule; a rotatable optical fiber that passes through the rotatable ferrule and the guide ferrule, wherein the rotatable optical fiber is secured within the rotatable ferrule and is free to rotate within the guide ferrule; and a sleeve that is configured to secure the guide ferrule and receive a static ferrule including a static optical fiber such that a face of the static optical fiber is brought into close proximity to a face of the rotatable optical fiber; wherein the method comprises: connecting the static optical fiber to the lens-less optical rotary joint by inserting the static ferrule into the sleeve to form a first connection; connecting the rotatable optics of the imaging probe to the rotatable optical fiber by coupling the rotatable optics into a rotatable optical connector to form a second connection; rotating the rotatable optical fiber and the rotatable optics; receiving a first signal from the static imaging device; transmitting the first signal to the rotatable optics through the first connection and the second connection during rotation of the rotatable optical fiber; and receiving a second signal from the imaging probe; and transmitting, simultaneously with transmission of the first signal, the second signal to the static imaging device through the first connection and the second connection during rotation of the rotatable optical fiber.

In some embodiments, the lens-less optical rotary joint further comprises a gap between the rotatable optical fiber and the static optical fiber.

In some embodiments, the gap has an index matching gel disposed therein.

In some embodiments, the gap has a width of less than 50 μm.

In some embodiments, the guide ferrule and the rotatable ferrule are separated by a spacing.

In accordance with some embodiments of the disclosed subject matter, a lens-less optical rotary joint is provided, the lens-less optical rotary joint comprising: means for positioning a rotatable optical fiber such that rotatable optical fiber is free to rotate within the means for positioning; means for securing the rotatable optical fiber; and means for securing the means for positioning such that the first optical fiber is coaxially aligned with a second optical fiber when means for securing the second optical fiber is inserted into the means for securing the means for positioning to bring a face of the first optical fiber into close proximity to a face of the second optical fiber.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

FIG. 2A shows an example of a coupling joint implemented using ferrules that can be used to implement a portion of an optical rotary joint in accordance with some embodiments of the disclosed subject matter.

FIG. 2B shows an example of an expanded view of a portion of the coupling joint shown in FIG. 2A in accordance with some embodiments of the disclosed subject matter.

FIG. 7A1 shows an example of a physical interface between a guide ferrule with an angled portion removed to set a reference face with a static ferrule in accordance with some embodiments of the disclosed subject matter.

FIG. 7B1 shows another example of a physical interface between a guide ferrule with an angled portion removed to set a reference face with a static ferrule in accordance with some embodiments of the disclosed subject matter.

FIG. 7C1 shows an example of a physical interface between a guide ferrule with a notch removed to set a reference face with a static ferrule in accordance with some embodiments of the disclosed subject matter.

FIG. 7D1 shows another example of a physical interface between a guide ferrule with a notch removed to set a reference face with a static ferrule in accordance with some embodiments of the disclosed subject matter.

FIG. 7E1 shows an example of a physical interface between a guide ferrule and a static ferrule with interlocking features in accordance with some embodiments of the disclosed subject matter.

FIG. 7F1 shows another example of a physical interface between a guide ferrule and a static ferrule with interlocking features in accordance with some embodiments of the disclosed subject matter.

FIGS. 7A2-7F2 show examples of alternate physical interfaces between a guide ferrule and a static ferrule in accordance with some embodiments of the disclosed subject matter.

DETAILED DESCRIPTION

In accordance with some embodiments of the disclosed subject matter, mechanisms (which can include systems and methods) for providing a rotary optical joint are provided.

In some embodiments, mechanisms described herein can be used to implement a multi-channel optical rotary joint. For example, in some embodiments, relatively high tolerance ferrules can be used to implement a "contact" optical fiber rotary joint, in which a pair of fibers are precisely aligned to maintain a face-to-face position at relatively high rotation speeds (e.g., on the order of thousands of revolutions per minute). In such an optical fiber rotary joint, a parallel off-set, angular mismatch and axial displacement between a rotatable optical fiber and static optical fiber can be minimized during rotation. In some embodiments, the mechanisms described herein can enable high efficiency transmission of optical power (signal) through a fiber core and inner cladding between a rotatable optical fiber and a static optical fiber with relatively low insertion loss and angular ripple during rotation.

In some embodiments, the mechanisms described herein can be used in applications that require multiple cladding fiber (e.g., double-cladding fiber, triple cladding fiber), which can be used, for example, in multimodality optical coherence tomography (OCT) imaging. For example, the single-mode fiber core can be used to transmit the OCT signal and/or excitation light of one or more add-on imaging modalities (e.g., fluorescence molecular imaging, fluorescence life-time imaging, multi-photon microscopy, or Raman spectroscopy). In such an example, the large surface area/high numerical aperture multimode inner-cladding of the fiber can be used for carrying excitation light and/or collecting signals captured by a probe, which can result in a relatively high optical damage threshold and improved signal collection efficiency. In many cases, use of an optical fiber rotary joint for multimodality OCT imaging requires stable high core-to-core, cladding-to-cladding efficiency, low core-cladding crosstalk transmission at relatively high rotation speeds. In some embodiments, an optical rotary junction implemented using the mechanisms described herein can be compatible with a variety of types of OCT, such as OCT, OCT+NIRS, OCT+NIRF, OCT+NIRAF, OCT+Raman, etc., which may typically use single mode fibers and/or multi-mode fibers.

Figure 1:
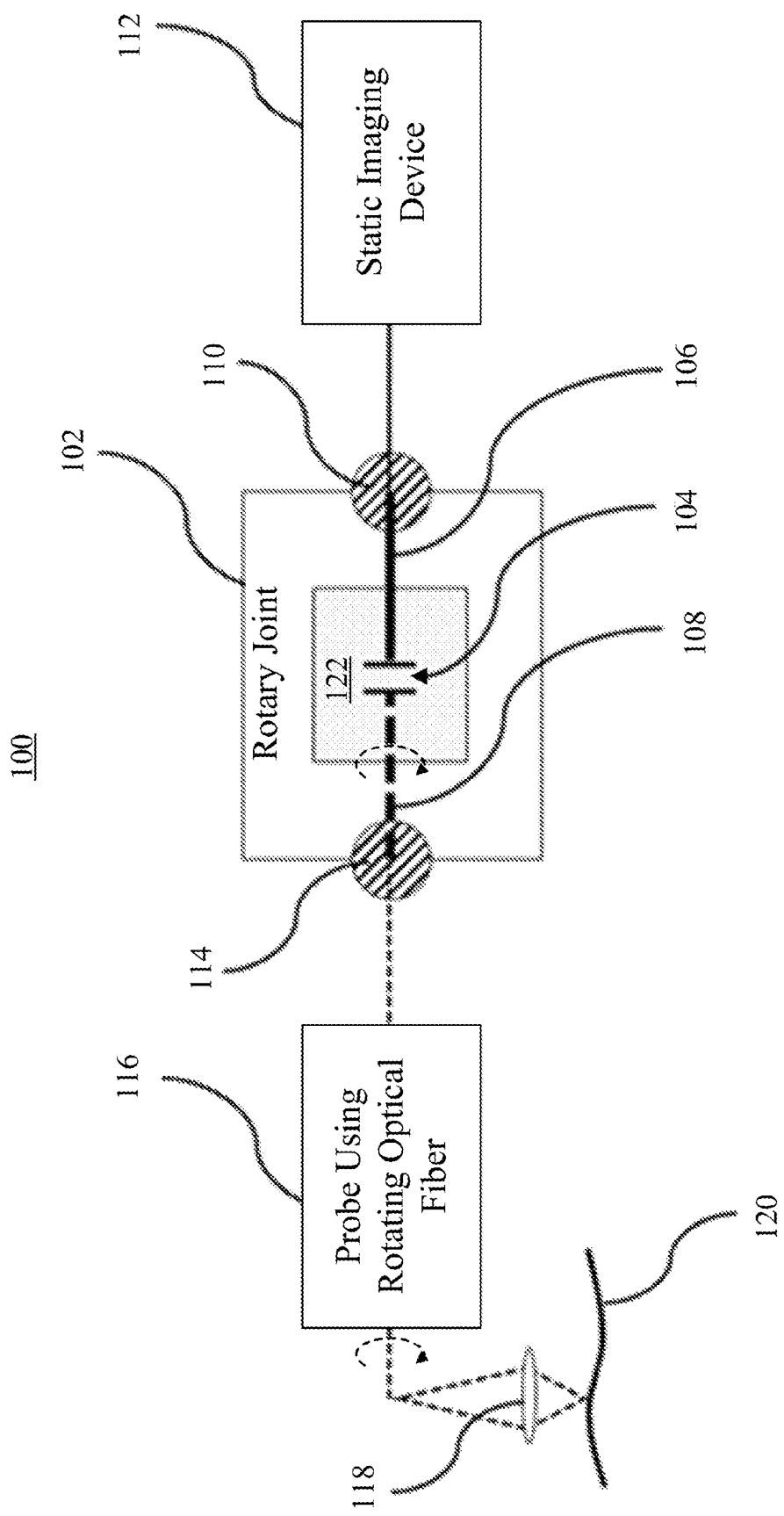
FIG. 1 shows an example of a system for providing an optical rotary joint in accordance with some embodiments of the disclosed subject matter.

FIG. 1 shows an example 100 of a system for providing an optical rotary joint in accordance with some embodiments of the disclosed subject matter. As shown in FIG. 1, a rotary joint 102 can be used to pass optical information between a static imaging device 112, and an imaging probe 116 using a rotatable optical fiber and/or optics to capture image data of a sample 120 (e.g., a portion of a subject's anatomy, such as the subject's esophagus, another portion of the subject's gastrointestinal tract, a blood vessel, a portion of the renal system, etc.). The static imaging device 112 may include a time-based detector that collects scanned information and processes the information to produce images. In some embodiments, imaging probe 116 can include a rotatable (or otherwise movable) fiber element that can change position with respect to sample 120 (e.g., to gather circumferential information from imagining probe 116). In some embodiments, a rotary joint implemented in accordance with some embodiments of the disclosed subject matter can operate over a wide range of wavelengths (e.g., any wavelengths supported by the fibers used to transmit the signals), such as from about 200 nanometers (nm) to about 1800 nm. Additionally, in some embodiments, multiple wavelengths can be simultaneously transmitted without incurring losses or distortions caused when lenses are used to attempt to focus a signal including multiple wavelengths.

In some embodiments, rotary joint 102 can pass information between a static fiber 106 and a moving fiber 108 via a coupling joint 104 (e.g., as described below in connection with FIGS. 2A and 2B). In some embodiments, rotary joint 102 can interface with static imaging device 112 via a static optical fiber connector 110, and can interface with imaging probe 116 via a moving optical fiber connector 114.

In some embodiments, one or more light sources within (or otherwise coupled to) static imaging device 112 provide light to static fiber 106 (e.g., via static optical fiber connector 110 and an optical fiber connecting static imaging device 112 to rotary joint 102). The light provided to static fiber 106 can be communicated from static fiber 106 to moving fiber 108 through coupling joint 104, and then can be provided from moving fiber 108 to imaging probe 116 (e.g., via moving optical fiber connector 114 and an optical fiber within imaging probe 116 that is configured to rotate). In various embodiments, imaging probe 116 can focus the light onto sample 120 using optics 118, and can capture light reflected and/or emitted by sample 120, and return the light along the same path back to static imaging device 112 (and/or another device via an optical splitter and/or other optics coupled to static imaging device 112 to transmit the return light to a different destination). In certain embodiments, rotary joint 104 can be at least partially lubricated by a fluid 122 that can reduce friction during rotation and/or reduce reflections at the face of the fibers.

FIG. 2A shows an example 200 of a coupling joint implemented using ferrules that can be used to implement a portion of an optical rotary joint in accordance with some embodiments of the disclosed subject matter. As shown in FIG. 2A, a rotary joint implemented in accordance with some embodiments of the disclosed subject matter can use three ferrules (during operation of the rotary joint) to implement a coupling joint (e.g., coupling joint 104). In some embodiments, coupling joint 200 can include a static ferrule 202, a guide ferrule 204, and a rotatable ferrule 208. In some embodiments, static ferrule 202 can be a portion of an optical fiber connector that is used to form an optical connection between a rotary joint and a static imaging device.

In some embodiments, a static optical fiber 210 can pass through at least a portion of static ferrule 202 to expose a face of static optical fiber 210 substantially near the end of static ferrule 202. Note that as described herein, static optical fiber 210 is not configured to rotate, but it may be connected and/or disconnected from the rotary joint and/or static imaging device. Additionally, in some embodiments, a rotatable optical fiber 212 can pass through rotatable ferrule 208 and at least a portion of guide ferrule 204 to expose a face of static optical fiber 210 substantially near the end of guide ferrule 204.

In certain embodiments, static ferrule 202 and guiding ferrule 204 can be coaxially aligned by a mating coupler 206. In some embodiments, mating coupler 206 can be implemented as a mating sleeve or other apparatus that has relatively high tolerances (i.e., at least inner dimensions that closely match the exterior dimensions of static ferrule 202 and guiding ferrule 204. In some embodiments, mating coupler 206 can have any suitable shape or combination of shapes. For example, mating coupler 206 can form a cylinder with an inner diameter that matches the exterior dimensions of ferrules with cylindrical bodies. As another example, mating coupler 206 can form a rectangular cuboid with interior dimensions that match the exterior dimensions of ferrules with a rectangular cross-sectional shape. As yet another example, mating coupler 206 can have multiple shapes to accommodate a static ferrule 202 that has a different exterior shape than guiding ferrule 204. In some embodiments, mating coupler 206 can be manufactured with relatively stringent tolerance requirements (e.g., approximately 1 µm).

As shown in FIG. 2A, static ferrule 202 and guiding ferrule 204 can include a through-hole having an inner diameter that is substantially similar to the outer diameter of an optical fiber to be passed through the ferrule (e.g., static optical fiber 210 and/or rotatable optical fiber 212). For example, each ferrule can have a through-hole with an inner diameter that leaves a buffer of about 0.5 to 1.0 micrometers (µm) (e.g., the inner diameter of static ferrule 202 and/or guiding ferrule 204 can be about 0.5 to 1.0 µm larger than the exterior diameter of the optical fiber that is to be inserted through the ferrules). For example, a buffer 218 can be provided around rotatable optical fiber 212 by guide ferrule 204. In such an example, the relatively small difference in diameters can facilitate alignment between static optical fiber 210 and rotatable optical fiber 212. As described above, static ferrule 202 and guide ferrule 204 can be aligned coaxially using mating coupler 206. In some embodiments, the ferrules used to implement the arrangement shown in FIG. 2A are high-tolerance ferrules (i.e., ferrules that are manufactured with relatively stringent tolerance requirements) that form a relatively tight fit with the interior of mating coupler 206. Guide ferrule 204 may be secured within mating coupler 206 permanently (e.g., by gluing with epoxy) or temporarily (e.g., using fasteners, such as screws).

In some embodiments, static optical fiber 210 can be stripped (e.g., to remove one or more layers, such as a cable jacket, a strength member, a coating, etc.) and secured within static ferrule 202 using any suitable technique or combination of techniques. For example, static optical fiber 210 can be secured within static ferrule 202 using epoxy 214. In some embodiments, after assembly of static optical fiber 210 and static ferrule 202, the end of the combined static optical fiber 210 and static ferrule 202 can be polished to provide a flat surface that can be closely mated with guide ferrule 204.

In various embodiments, rotatable optical fiber 212 can be stripped to a length that is substantially longer than the length of rotatable ferrule 208. In some such embodiments, rotatable optical fiber 212 can be inserted through rotatable ferrule 208 and secured within rotatable ferrule 208 using any suitable technique or combination of techniques. For example, rotatable optical fiber 212 can be secured within rotatable ferrule 208 using epoxy 216. In some embodiments, an end of rotatable optical fiber 212 can be inserted at least partially through guide ferrule 204 without being secured such that rotatable optical fiber can freely rotate with respect to guide ferrule 204.

In some embodiments, a spacing 220 (e.g., having a width W less than about 50 μm) between guide ferrule 204 and rotatable ferrule 208 can allow for some axial misalignment between guide ferrule 204 and rotatable ferrule 208, since rotatable optical fiber 212 can flex slightly (while still being rotatable) at the point of spacing 220. For example, a larger spacing 220 can allow for more misalignment without an unacceptable amount of distortion as the slope of rotatable optical fiber 212 between guide ferrule 204 and rotatable ferrule 208 is smaller for any given amount of misalignment. Accordingly, while a smaller spacing 220 may provide more consistent light transmission (e.g., with less distortion caused by vibration of rotatable optical fiber 212), a smaller spacing 220 also may require higher tolerance parts and/or more careful/time intensive assembly to insure a closer axial alignment between guide ferrule 204 and rotatable ferrule 208. On the other hand, a spacing 220 having a larger gap may allow for lower tolerance parts but may result in some additional distortion in image data sent over rotatable optical fiber 212 (e.g., due to vibration of rotatable optical fiber 212 caused by the misalignment). In some embodiments, spacing 220 can be any suitable gap, from on the order of micrometers to on the order of millimeters. For example, in some embodiments spacing 220 can be on the order of tens of micrometers. As another example, spacing 220 can be on the order of thousands of microns (i.e., millimeters). In a more particular example, spacing 220 can be from about 10 μm to about 5 mms. In another more particular example, spacing 220 can be from about 10 μm to about 50 μm. In yet another more particular example, spacing 220 can be from about 50 μm to about 1 mm. In still another more particular example, spacing 220 can be from about 1 mm to about 5 mm. In a further more particular example, spacing 220 can be from about 1.5 mm to about 3.5 mm.

In some embodiments, ferrules 202, 204, and 208 can be made from any suitable material, such as zirconia (and/or other ceramic materials), stainless steel, ruby, sapphire, any hard material (e.g., on order of the same hardness as the preceding materials) presenting a low attrition coefficient, or combinations thereof.

FIG. 2B shows an example 230 of an expanded view of a portion of the coupling joint shown in FIG. 2A (indicated by the dashed-line box in FIG. 2A) in accordance with some embodiments of the disclosed subject matter. As shown in FIG. 2B, in some embodiments, rotatable optical fiber 212 can be advanced through guide ferrule 204 such that a gap 232 of about 10 μm to about 50 μm is provided between the face of rotatable optical fiber 212 and the face of static optical fiber 210 during operation. That is, the face of rotatable optical fiber 212 is proximate the face of static optical fiber 210 but the faces of the two opposing fibers are not in contact. Note that a smaller gap 232 between the face of rotatable optical fiber 212 and the face of static optical fiber 210 generally results in better optical coupling between rotatable optical fiber 212 and static optical fiber 210.

Although the gap was described above as being between about 10 μm to about 50 μm, the gap can be any suitable length, such as between about 5 μm to about 100 μm, between about 10 μm to about 75 μm, between about 25 μm to about 50 μm, less than about 100 μm, less than 75 μm, less than 100 μm, etc.

In some embodiments, gap 232 can be filled with a transmission fluid 234, which can also, in some embodiments, fill buffer 218 to reduce friction during rotation of rotatable optical fiber 212. In some embodiments transmission fluid 234 can be a fluid with optical transmission properties that increase throughput of light through gap 232. For example, transmission fluid 234 can be an index matching gel that reduces reflections at the interface between the optical fibers and gap 232 compared to reflections that would be present if gap 232 were filled with air or other medium. In a more particular example, an index matching gel that has a refractive index that is relatively close to the fiber core and that produces low fluorescence can be used. Additionally or alternatively, in some embodiments, one or more anti-reflection coatings can be applied on the exposed faces of one or both of the static optical fiber 210 and rotatable optical fiber 212.

In some embodiments, for example as described in more detail below in connection with FIGS. 7A to 7F, guide ferrule 204 can include one or more reference edges, such as reference edge 236, the size and/or shape of which can be used set the width of gap 232. For example, using such a reference edge can facilitate the use of different static connectors with different ferrule assemblies and/or the removal and reconnection of static ferrule 202, while providing a consistent gap width which can contribute to consistent performance. In some cases, removal of the static ferrule can facilitate maintenance. Note that, in some embodiments, transmission fluid 234 can be replenished periodically (e.g., when static ferrule 202 is introduced into mating coupler 206). For example, transmission fluid 234 can have a relatively high viscosity, and at least some transmission fluid 234 can remain in proximity to a face of guide ferrule 204 when static ferrule 202 is removed. However, a portion of transmission fluid 234 may be removed with static ferrule 202. In some embodiments, one or more faces of the rotatable optical fiber and/or the static optical fiber can be coated with a low friction material (e.g., polytetrafluoroethylene, sold under the brand name Teflon®) to reduce friction at any interface between two optical fiber. In some embodiments, the diameter of the fibers near the faces of rotatable optical fiber 212 and static optical fiber 210 can be slightly enlarged to create a larger optical interface, which may reduce potential losses from misalignment.

Figure 3:
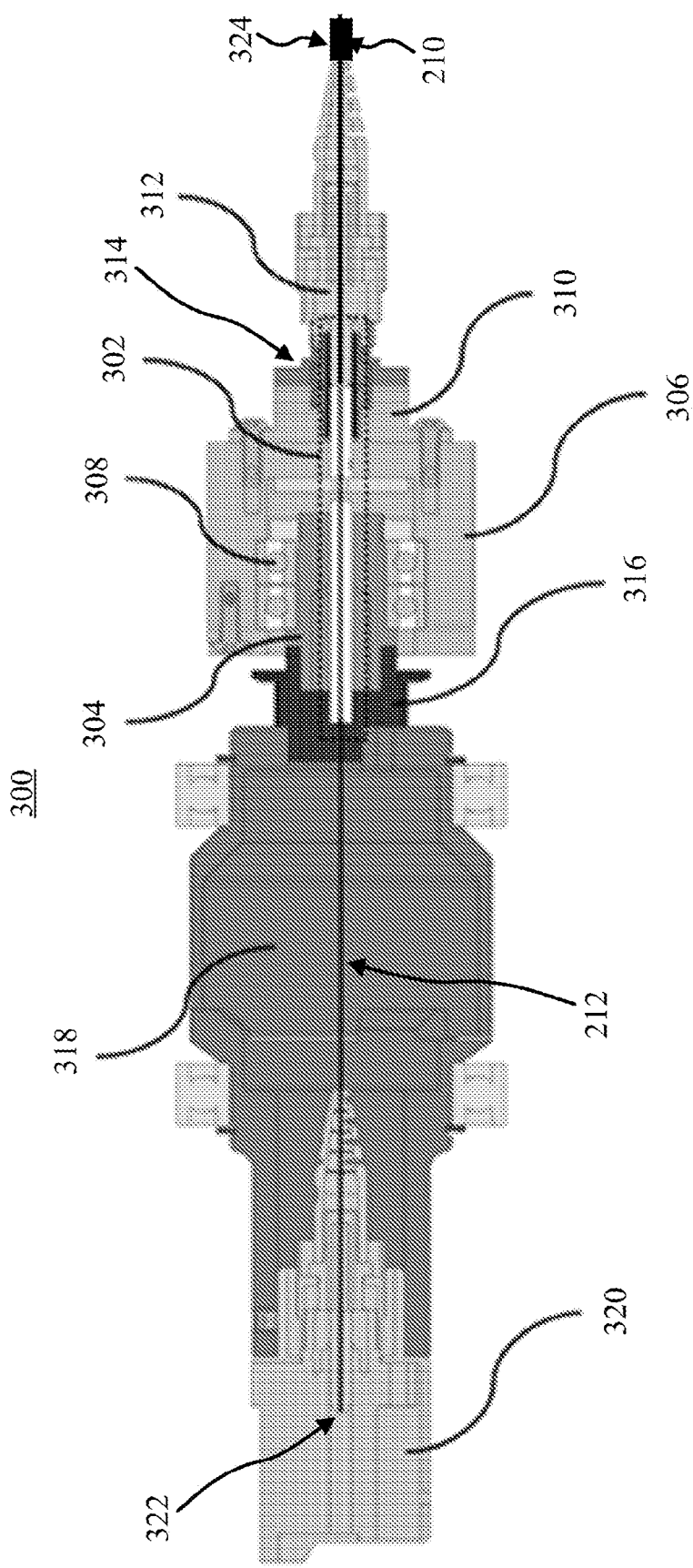
FIG. 3 shows an example of a cross section of an optical rotary joint in accordance with some embodiments of the disclosed subject matter.

FIG. 3 shows an example 300 of a cross-section view of an optical rotary joint in accordance with some embodiments of the disclosed subject matter. As shown in FIG. 3, optical coupling can occur within optical rotary joint 300 in a central portion 302 (shown by dotted-line box) that can, for example, be implemented using coupling joint 200 described above in connection with FIGS. 2A and 2B.

In some embodiments, rotatable fiber 212 can be secured within a rotatable ferrule (e.g., rotatable ferrule 208, as described above in connection with FIG. 2A), which can be coupled to a shaft 304, such that rotation of shaft 304 causes rotation of rotatable optical fiber 212 (e.g., via rotatable ferrule 208). Alternatively, in some embodiments, rotatable fiber 212 can be coupled to shaft 304 using any other suitable technique or combination of techniques. For example, rotatable fiber 212 can be secured within a through-hole in shaft 304 (e.g., of a similar size to the through-hole in rotatable ferrule 208). This may require that, for example, shaft 304 be manufactured with more stringent tolerances.

In some embodiments, shaft 304 can rotate within a static housing 306 (i.e., housing 306 is not configured to rotate with shaft 304) using bearings 308 and/or any other suitable components that sufficiently reduce friction during rotation of shaft 304.

As shown in FIG. 3, static optical fiber 210 can be secured within a connector 312 that includes a ferrule (e.g., static ferrule 202), which can be used to provide an interface between a fiber optic cable 324 that includes static optical fiber 210 and optical rotary joint 300. In some embodiments, connector 312 can be physically coupled to optical rotary joint 300 via a connector position system that is maintained in a particular relationship with coupling joint 302 via an adapter plate 314 that is physically coupled to optical rotary joint 300 by an adapter component 310. In some embodiments, adapter component 310 and/or adapter plate 314 can be replaceable to facilitate the use of fiber optic connectors that are configured to use different connection mechanisms.

In some embodiments adapter component 310 can axially align static optical fiber 210 and rotatable optical fiber 212, for example, by precisely aligning static ferrule 202 and guide ferrule 204. In some embodiments, mating coupler 206 can be incorporated into adapter component 310 and/or adapter plate 314, and/or securely coupled to adapter component 310 and/or adapter plate 314 (e.g., by one or more fasteners, by one or more substances such as epoxy, by friction, by interlocking components, etc.).

In some embodiments, shaft 304 can be coupled to a motion coupling device 316, which can, for example, be coupled to a motor, e.g., via a timing belt pulley, a v-belt pulley, or other components that can be used to convey torque from the motor or other motion inducing apparatus to motion coupling device 316.

In some embodiments, rotatable fiber 212 extends from rotatable ferrule 208 to a rotatable optical fiber connector 320 through a fiber drum 318 and can terminate at a face 322. In some embodiments, fiber drum 318 can provide protection for rotatable optical fiber 212 from other portions of optical rotary joint 300 during operation (i.e., while rotatable optical fiber 212 is being rotated). In some embodiments, a connector from an imaging device (e.g., probe 116) that includes a rotatable optical fiber can be optically coupled to rotatable optical fiber 212 via rotatable fiber optic connector 320 to create an optical connection between the probe and rotatable optical fiber 212 at face 322. Additionally, in some embodiments, rotatable optical connector 320 can be coupled to shaft 304 such that rotation of shaft 304 rotates rotatable optical fiber 212 and a rotatable optical fiber included in the probe at the same rate. In some embodiments, fiber drum 318 can rotate at the same rate as rotatable optical fiber 212 to provide protection for rotatable optical fiber 212 during operation, and in some embodiments, to provide a mechanical link between shaft 304 and rotatable optical fiber connector 320. In some embodiments, drum 318 can be generally hollow. Note that, although not shown, an optical rotary joint implemented in accordance with some embodiments of the disclosed subject matter can include one or more rotatable electric connections. For example, some imaging probes with rotatable optics may also include electronics which connect through a rotatable tether, and the optical rotary joint can be configured to provide rotatable electric connections to send electronic signals to and/or from the imaging probe.

Figure 4:
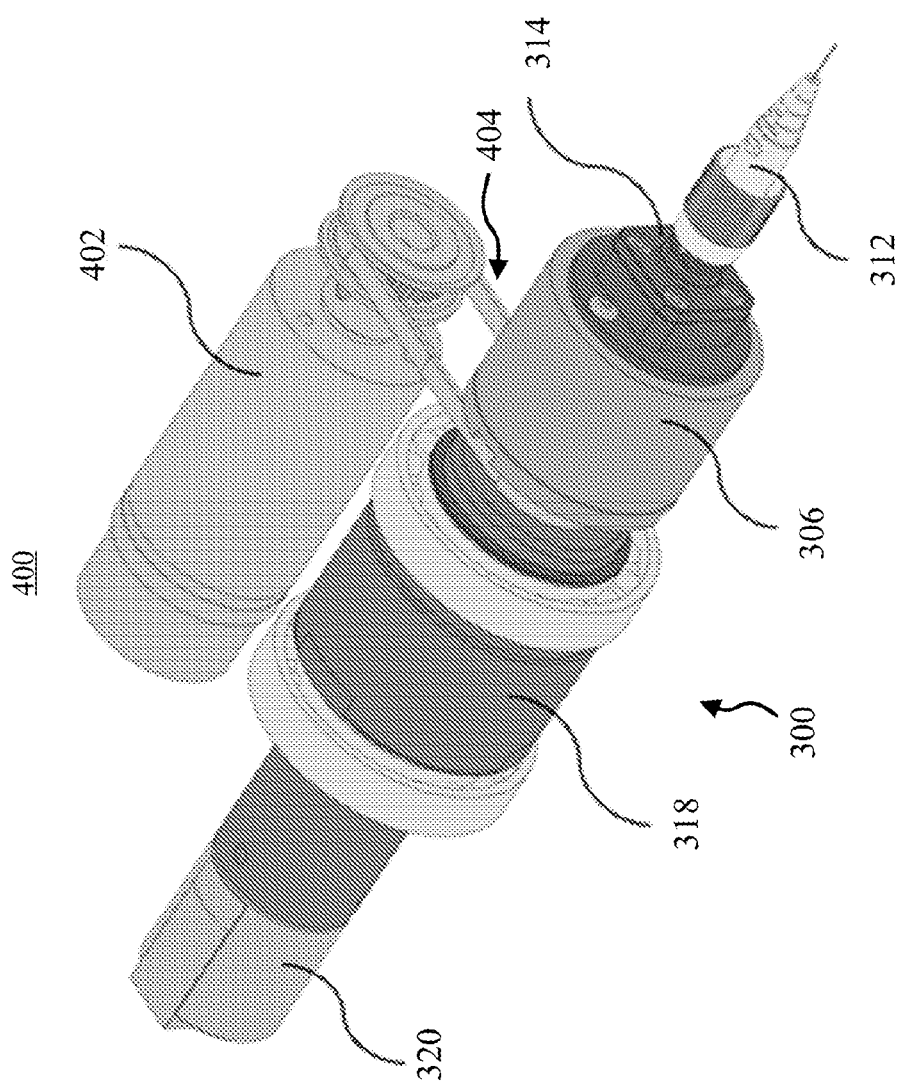
FIG. 4 shows an example of an optical rotary joint coupled to a motor in accordance with some embodiments of the disclosed subject matter.

FIG. 4 shows an example 400 of an optical rotary joint coupled to a motor in accordance with some embodiments of the disclosed subject matter. As shown in FIG. 4, a motor 402 can be coupled to optical rotary joint 300 via a timing belt 404. In some embodiments, when motor 402 is in operation to rotate a rotatable optical fiber (e.g., rotatable optical fiber 212), the exterior of housing 306 can remain stationary, while a shaft and bearing assembly (e.g., including shaft 304 and bearings 308) rotates within housing 306.

As shown in FIG. 4 and described above in connection with FIG. 3, connector 312 can be physically coupled to optical rotary joint 300 via adapter plate 314. Although a particular type of optical connector is shown in FIG. 4, this is merely an example, and adapter plate 314 can be configured to couple to any suitable optical connector (e.g., such as a standardized optical connector, a custom optical connector, and/or a future optical connector).

Note that, FIG. 4 shows motor 402 and optical rotary joint 304 as being separate devices coupled via timing belt 404, this is merely an example, and in certain embodiments motor 402 can be configured as a direct drive motor, such as a hollow core motor through which rotatable optical fiber 212 passes.

In some embodiments, motor 402 can be controlled by the static imaging system. For example, the rotational speed of motor 402 (e.g., denoted in revolutions per minute) can be controlled based on a voltage signal received over an electrical (or wireless) connection with the static imaging device. Additionally or alternatively, motor 402 can be controllable via controls that are separate from the static imaging device (e.g., controls integrated into optical rotary joint 300 and/or motor 402, controls provided via an application being executed by a computing device such as a smartphone, tablet, laptop computer, etc., and communicated to motor 402 via a wired and/or wireless link, etc.). In some embodiments, an optical rotary joint implemented in accordance with some embodiments of the disclosed subject matter can be operated at a wide range of rotational speeds, for example, from single digit or lower revolutions per minute (RPM) up to tens of thousands of revolutions per minute, which may be limited by the tolerances of the bearings or other friction reducing elements used, and the alignment of the components, but may not be limited by friction between the rotatable optical fiber and the static optical fiber. For example, an optical rotary joint implemented in accordance with some embodiments of the disclosed subject matter can be operated at 6,000 RPM, 12,000 RPM, 18,000 RPM, or 24,000 RPM.

Figure 5A:
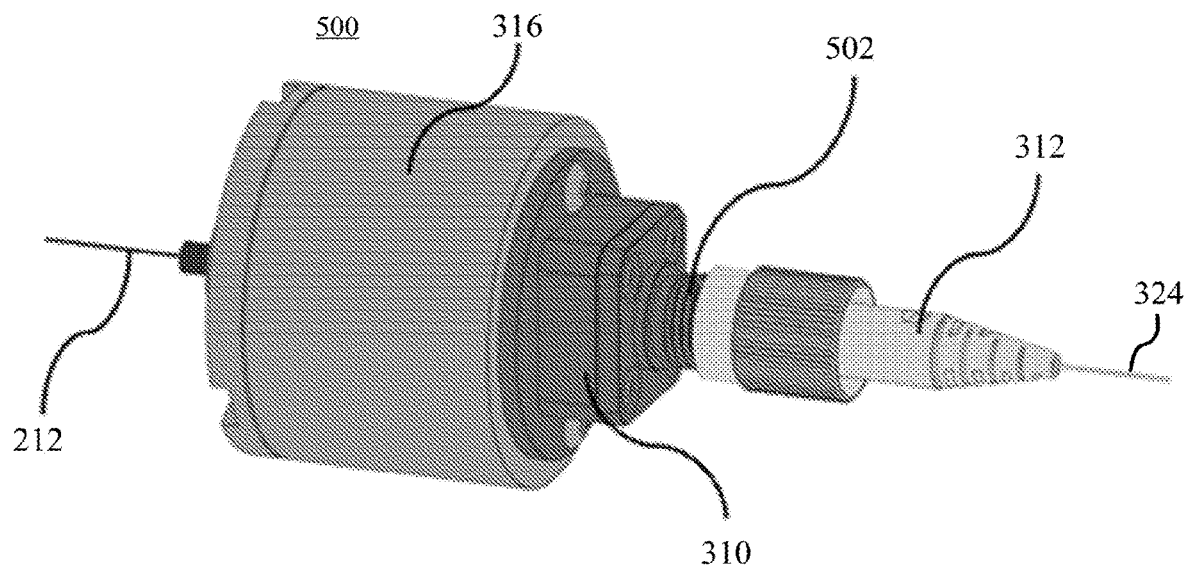
FIG. 5A shows an example of a connection between an optical rotary joint and a static imaging device in accordance with some embodiments of the disclosed subject matter.

FIG. 5A shows an example 500 of a connection between an optical rotary joint and a static imaging device in accordance with some embodiments of the disclosed subject matter. As shown in FIG. 5A, connector 312 can be coupled to adapter component 310 via a standardized connector such as a threaded, screw-in connection such as an FC/PC receptacle 502, which facilitates easy connection and disconnection of the optical rotary joint with various static imaging devices (e.g., static imaging device 112). In the example shown in FIG. 5A, connector 312 can be aligned with the optical rotary joint by FC/PC receptacle 502 such that the static fiber (e.g., static fiber 210 within fiber optic cable 324) is axially aligned with the rotatable optical fiber. In the example shown in FIG. 5A, the connector is relatively low cost, and easily replaced if the connector or cable should become damaged, as it is a standardized fiber optic connector. However, the example shown in FIG. 5A may be more susceptible to poor alignment, the introduction of foreign objects (e.g., dust) into coupling device 316, or other complications, many of which may be caused by unintended use by an operator.

Figure 5B:
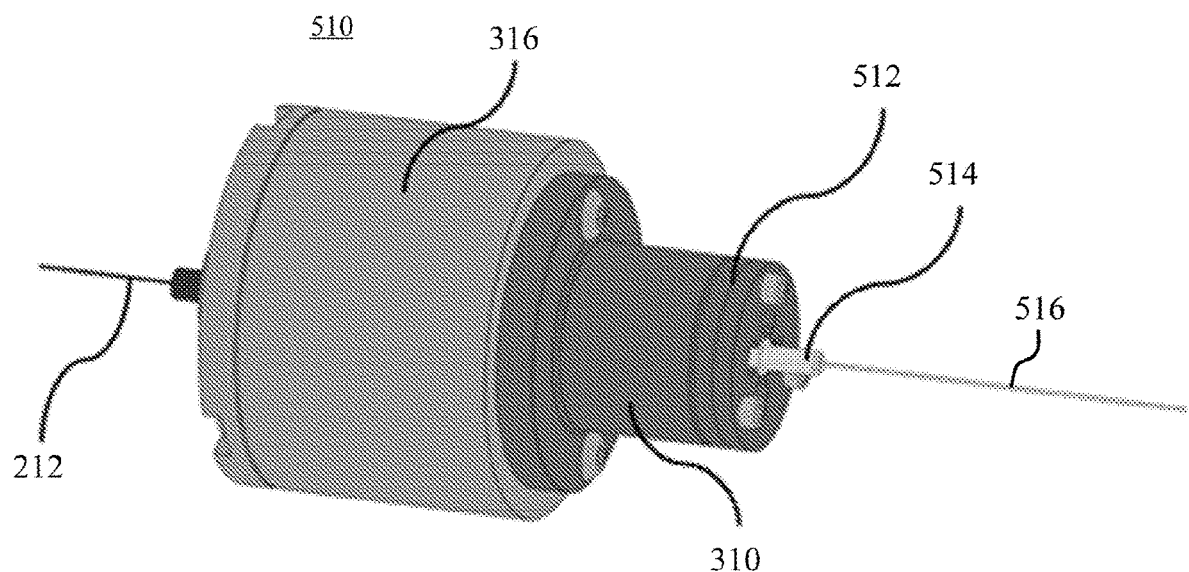
FIG. 5B shows another example of a connection between an optical rotary joint and a static imaging device in accordance with some embodiments of the disclosed subject matter.

Thus, FIG. 5B shows another example 510 of a connection between an optical rotary joint and a static imaging device in accordance with some embodiments of the disclosed subject matter. As shown in FIG. 5B, an intermediate connector 514 can be more permanently coupled to the optical rotary joint via an adapter plate 512 coupled to an adapter component 310. In the example shown in FIG. 5B, information (e.g., optical information) can be passed through an optical connection formed within coupling device 316 between a static optical fiber (e.g., static optical fiber 210 included in a fiber optic cable 516) and rotatable optical fiber 212. Connector 514 in FIG. 5B can be isolated within the optical rotary joint to reduce the likelihood of later misalignment or the introduction of foreign objects into the optical rotary joint. In some embodiments, connector 514 can be permanently or semi-permanently (e.g., via fasteners) coupled to optical rotary joint 510, rather than using connector 312 that is configured to be attached and detached relatively easily.

Figure 6A:
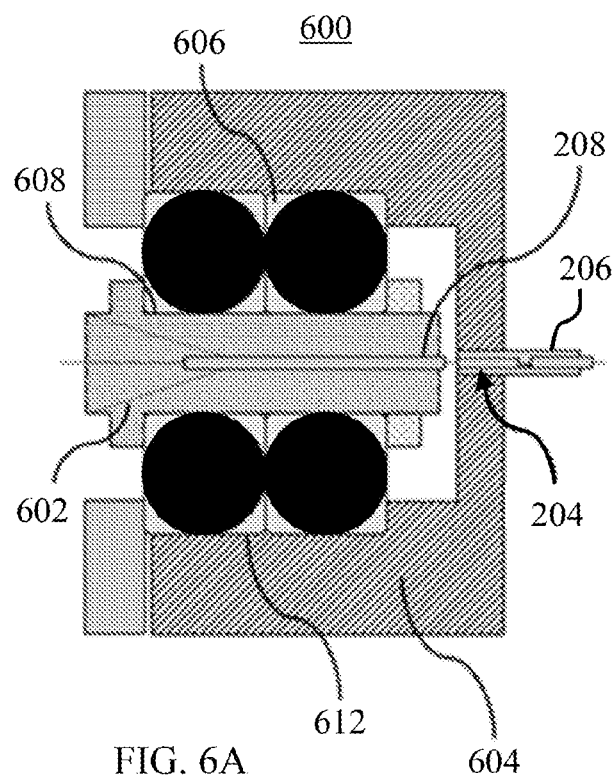
FIG. 6A shows an example of a portion of a housing for an optical rotary joint in accordance with some embodiments of the disclosed subject matter.

FIG. 6A shows an example 600 of a portion of a housing for an optical rotary joint in accordance with some embodiments of the disclosed subject matter. As shown in FIG. 6A, a single piece housing 604 can be used to secure and align various components of the optical rotary joint. For example, housing 604 can be a made using relatively stringent tolerances, which can cause housing 604 to be relatively costly to manufacture. In some embodiments, a shaft 602 (e.g., shaft 304) can rotate within housing 604 via bearing 606 (e.g., implemented using high prevision bearings). In some embodiments, bearings 606 can be implemented as any suitable type of bearing, such as ball bearings or roller bearings. In the example shown in FIG. 6A, both shaft 602 and housing 604 may be required to be manufactured with relatively stringent tolerances to insure that shaft 602/rotatable ferrule 208 are axially aligned with guide ferrule 204. Shaft 602 has critical faces 608 where it mates with bearings 606 and where it mates with rotatable ferrule 208, and housing 604 has critical faces 612 where it meets with bearings 606 and where it mates with mating coupler 206. In some embodiments, housing 604, shaft 602, and ferrules 204 and 208 may be required to be manufactured with relatively strict dimensional tolerances of the various critical faces and concentricity of features (e.g., on the order of 1 µm).

Figure 6B:
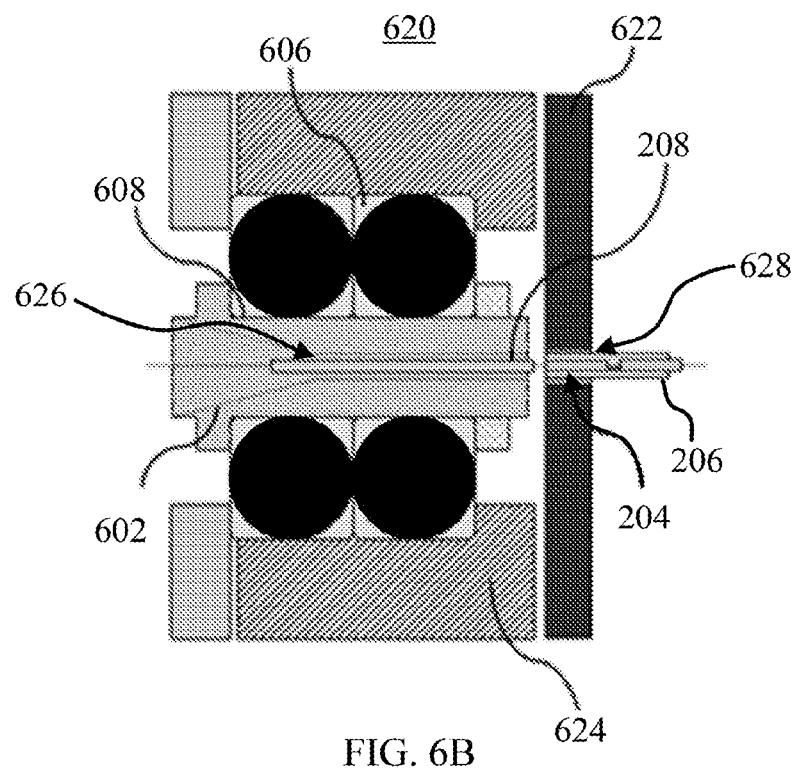
FIG. 6B shows another example of a portion of a housing for an optical rotary joint in accordance with some embodiments of the disclosed subject matter.

FIG. 6B shows another example 620 of a portion of a housing for an optical rotary joint in accordance with some embodiments of the disclosed subject matter. As shown in FIG. 6B, housing 620 can be implemented using multiple portions such as a shaft housing 624 and an optical joint housing 622, which can be used to secure and align various components of the optical rotary joint. In the example shown in FIG. 6B, housing 620 can be made using relatively less stringent tolerances, which can cause housing 620 to be relatively less costly to manufacture. In some embodiments, guide ferrule 204 can be coupled to optical joint housing 622, which can be configured to be adjustable with respect to shaft housing 624.

In some embodiments, shaft 602 in the example shown in FIG. 6B only has a critical face 608 where it mates with bearings 606, and rotatable ferrule 208 can be actively aligned within shaft 602 by setting it within a relatively large bore hole 626. In some embodiments, such an active alignment process can ensure that rotary ferrule 208 spins coaxially with the bearings (i.e., that rotary ferrule 208 is centered within bearings 606 and is parallel with the axis of rotation of bearings 606). In some embodiments, housing 620 can be manufactured without using relatively high tolerance parts, such as by splitting housing 624 into two separately adjustable parts, or by implementing housing 624 using a v-groove mechanism to secure bearings 606.

In some embodiments, optical coupling for an optical rotary joint implemented using housing 620 can occurs within optical joint housing 622, which can be implemented with elements that facilitate alignment with the true center of rotatable ferrule 208. In some embodiments, adjustment screws can be used to align parts of housing 620 (e.g., by using high precision adjustment screws).

In some embodiments, the stringency of the tolerances of optical joint housing 622 can be further reduced by actively aligning guide ferrule 204 by positioning mating coupler 206 within a large bore 628. Note that, although the cost of manufacturing components of housing 620 will be generally lower than the cost of manufacturing components of housing 600, assembly of the components of housing 620 may be more time intensive and/or more complicated. For example, assembly may require the use of many jigs.

FIGS. 7A1-7F2 show examples physical interfaces between a guide ferrule and a static ferrule in accordance with some embodiments of the disclosed subject matter. As described above, an optical rotary joint implemented using mechanisms described herein can obviate the need for collimation or other lensing elements within the coupling joint. In some embodiments, in order to achieve sufficient coupling between static optical fiber 210 and rotatable optical fiber 212, the gap (e.g., gap 232) between the flat faces of static optical fiber 210 and rotatable optical fiber 212 can be minimized. While in an infinitely rigid motion system, the gap can theoretically be reduced to zero thickness, in practice some space (e.g., on the order of 20-50 µm) is desired to allow for small axial translation between fiber faces. In some embodiments, any suitable technique or combination of techniques can be used to implement a repeatable gap between fiber faces for ease of assembly/reassembly and servicing of the optical rotary joint. For example, as shown in FIG. 7A1, in an example configuration 700 an angled portion of static ferrule 202 and/or guide ferrule 204 can be removed (e.g., by polishing). In such an example, the polish can create a reference face 704 at which static ferrule 202 makes contact with guide ferrule 204, which can create a cavity 702 when assembled. As another example, FIG. 7B1 shows another example configuration 710 in which a larger portion of guide ferrule 204 has been removed (e.g., by polishing). In such an example, the polish can create a reference face 714 at which static ferrule 202 makes contact with guide ferrule 204, which can create a larger cavity 712 when assembled. In such an example, the larger polish can allow rotatable optical fiber 212 to flex during rotation, and can also allow for more transmission fluid to be used within the coupling joint, which may be desirable in some cases.

As yet another example, FIG. 7C1 shows an example configuration 720 in which a notch 722 has been removed from guide ferrule 204 (e.g., by milling or boring) to create a reference face 724. As shown in FIG. 7C1, notch 722 can be implemented as a step, which can create a relatively more uniform referencing between static ferrule 202 and guide ferrule 204 in comparison to the reference faces shown in FIGS. 7A1 and 7B1, but which may require more precision than the removal of an angled portion as shown in FIGS. 7A1 and 7B1.

As still another example, FIG. 7D1 shows an example configuration 730 in which a notch 732 has been removed from guide ferrule 204 (e.g., by milling or boring) to create reference faces 734 around the periphery of guide ferrule 204. As shown in FIG. 7D1, notch 732 can be implemented as a slot/bore, which can create a relatively more uniform referencing between static ferrule 202 and guide ferrule 204 in comparison to the reference faces shown in FIGS. 7A1 and 7B1, but which may require more precision than the removal of an angled portion as shown in FIGS. 7A1 and 7B1.

As a still further example, FIGS. 7E1 and 7F1 show example configurations 740 and 750 in which interlocking features between guide ferrule 204 and static ferrule 202 are created. As shown in FIGS. 7E1 and 7F1, such interlocking features can create different reference faces 744 or 754 based on the orientation of guide ferrule 204 and static ferrule 202, which can be used to change the gap between rotatable optical fiber 212 and static optical fiber 210 by indexing the angle of the static ferrule. In some embodiments, the gap can be set to be relatively large 742 or closer 752, or any other distance that can be set by the interlock geometry. In some embodiments, a greater number of reference face sets can be used to facilitate more finely grained gap adjustments, but may increase manufacturing complexity. Although FIGS. 7A1-7F1 were generally described above as being implemented by modifying the face of guide ferrule 204, this is merely an example, and as shown in FIGS. 7A2-7F2, corresponding changes can be made to the face of static ferrule 202, in addition to, or in lieu of, changing the face of guide ferrule 204.

Figure 8A:
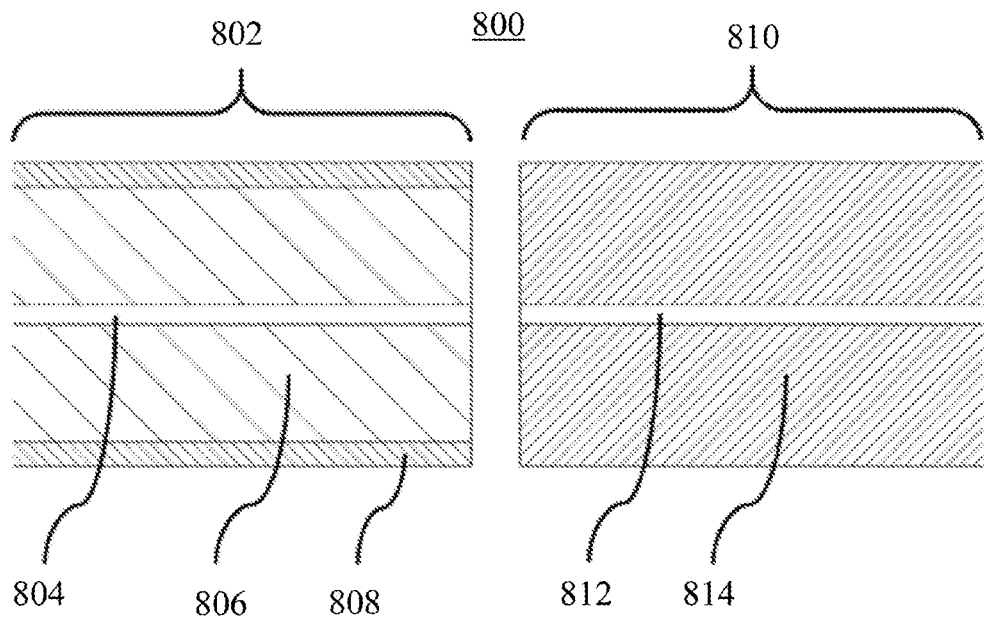
FIG. 8A shows an example of an interface between a double clad optical fiber and a single-mode optical fiber that can be created within a rotary optical joint in accordance with some embodiments of the disclosed subject matter.

FIG. 8A shows an example 800 of an interface between a double clad optical fiber and a single-mode optical fiber that can be created within a rotary optical joint in accordance with some embodiments of the disclosed subject matter. In some embodiments, rotatable optical fiber 212 can be implemented using a double clad fiber (DCF) 802 that includes a core 804, an inner cladding 806, and (in some cases) a buffer 808. In some embodiments, separate signals can be sent using core 804 and inner cladding 806. However, as shown in FIG. 8A, static optical fiber 210 can be implemented as a single mode fiber 810 that includes a core 812, and a non-light transmitting cladding 814. In such a single mode fiber, information can only be sent between matching cores (e.g., between core 804 and core 812). Note that, although rotatable optical fiber 212 is shown in FIG. 8A as being a DCF, a static imaging device configured to use only a single mode fiber can be used in connection with the optical rotary joint, as DCF 802 can act as a SMF by only utilizing core 804 for signal transmission. In some such embodiments, the signal carrying potential of the optical rotary joint may be fully utilized, but it does not lose efficiency in comparison to a lens-based rotary junction that uses exclusively SMF.

Figure 8B:
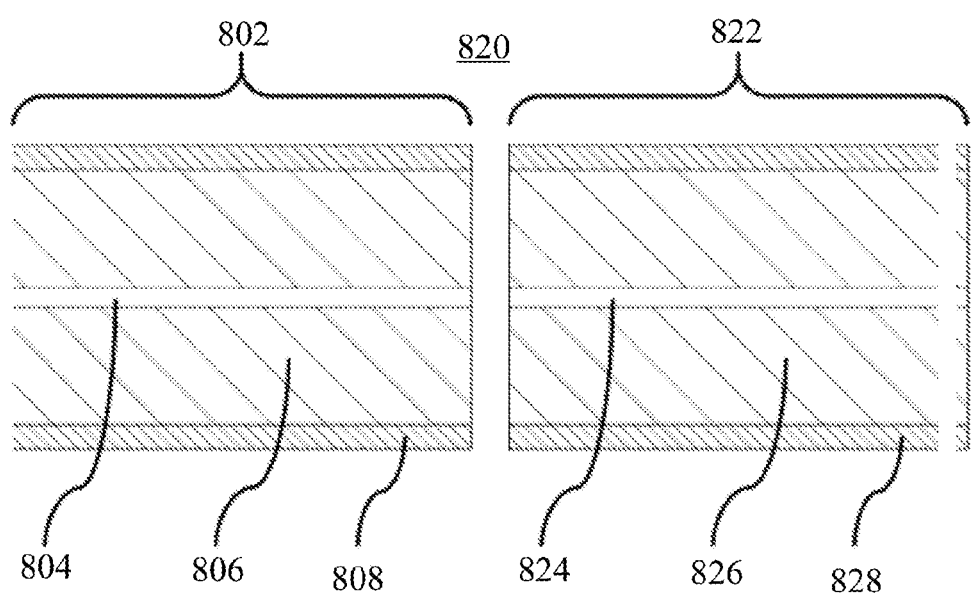
FIG. 8B shows an example of an interface between two double clad optical fibers that can be created within a rotary optical joint in accordance with some embodiments of the disclosed subject matter.

FIG. 8B shows an example 820 of an interface between two double clad optical fibers that can be created within a rotary optical joint in accordance with some embodiments of the disclosed subject matter. In some embodiments, rotatable optical fiber 212 and static optical fiber 210 can be implemented using DCF 802, and static optical fiber 210 can be implemented using a DCF 822 that includes a core 824, an inner cladding 826, and (in some cases) a buffer 828. In some embodiments, separate signals can be sent using cores 804 and 824, and inner claddings 806 and 826.

Figure 9:
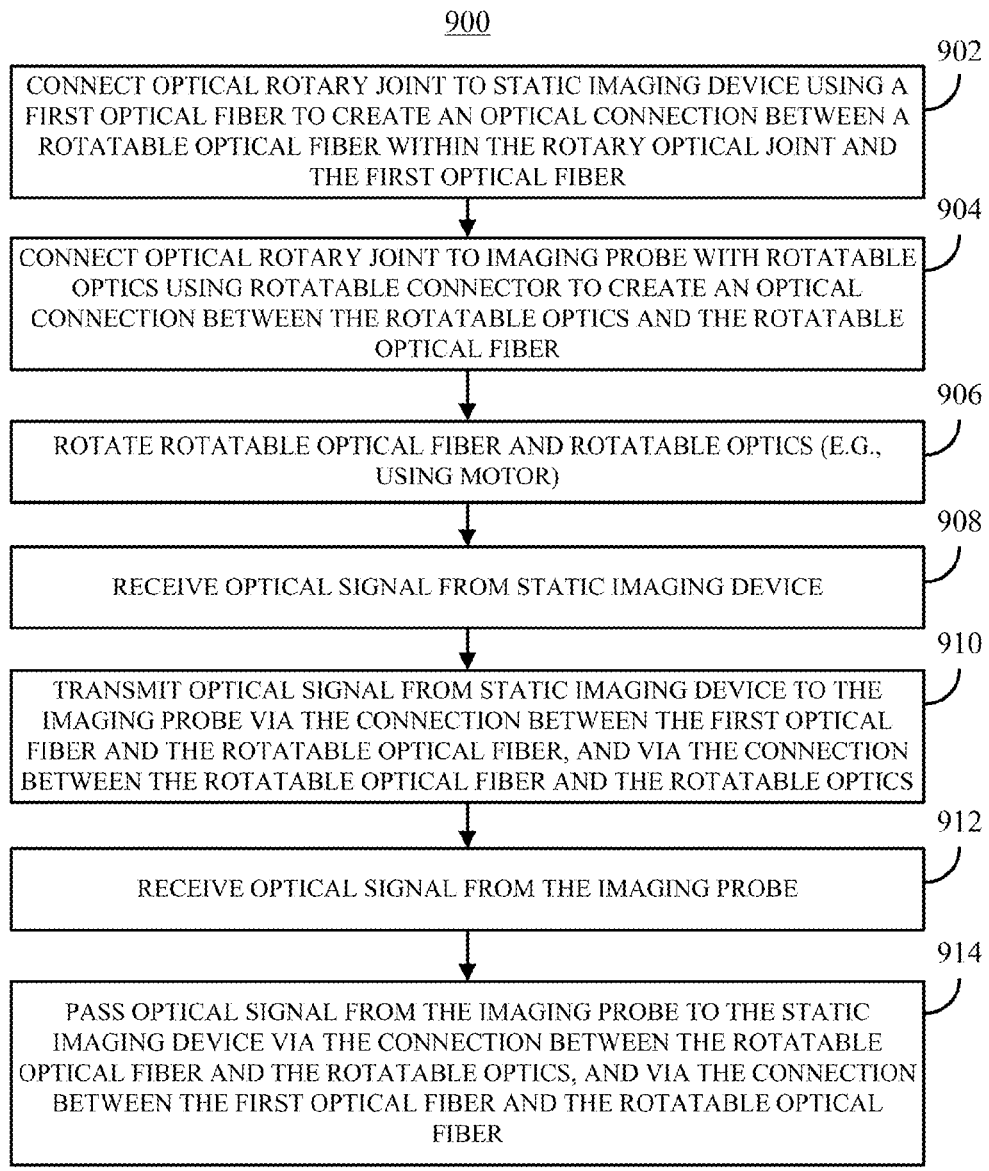
FIG. 9 shows an example of a process for providing an optical connection between a static imaging device and a probe with rotatable optics using an optical rotary joint in accordance with some embodiments of the disclosed subject matter.

FIG. 9 shows an example 900 of a process for providing an optical connection between a static imaging device and a probe with rotatable optics using an optical rotary joint in accordance with some embodiments of the disclosed subject matter. As shown in FIG. 9, at 902, process 900 can include connecting an optical rotary joint implemented in accordance with some embodiments of the disclosed subject matter (e.g., as described above in connection with FIGS. 1-8) to a static imaging device using a first optical fiber (e.g., a fiber optic cable that includes a single-mode fiber, a double clad fiber, etc.) via a first connector to create an optical connection between a rotatable optical fiber within the rotary optical joint and the first optical fiber. As described above in connection with FIGS. 2A and 2B, for example, the two optical fibers can form an optical connection with a small gap (e.g., on the order of tens of micrometers) by mating the end of a ferrule that encloses the first optical fiber and a guide ferrule that positions (but does not secure) the rotatable optical fiber.

At 904, process 900 can include connecting the optical rotary joint to an imaging probe with rotatable optics using a rotatable connector to create an optical connection between the rotatable optics of the probe and the rotatable optical fiber of the optical rotary joint. As described above (e.g., in connection with FIG. 3), a rotatable connector can couple the rotatable optics of the probe to the rotatable optical fiber of the optical rotary joint such that an optical connection is established and maintained during rotation, and such that the rotatable optics are rotated at the same rate as the rotatable optical fiber.

At 906, process 900 can include rotating the rotatable optical fiber and the rotatable optics. For example, as described above in connection with FIGS. 3 and 4, a motor can be coupled to the rotatable optical fiber via a motion coupling device (e.g., motion coupling device 316), a shaft (e.g., shaft 304) connected to the motion coupling device, and a ferrule (e.g., rotatable ferrule 208) secured within the shaft and within which the rotatable optical fiber is secured. At 906, rotation of the motor can also cause rotation of the rotatable optics within the probe via the motion coupling device, and a fiber drum (e.g., fiber drum 318) that provides a physical coupling between the motion coupling device and the rotatable connector to rotate the rotatable connector, which in turn causes rotation of the rotatable optics.

At 908, process 900 can include receiving an optical signal from the static imaging device at the rotary optical joint. For example, the static imaging device can include one or more light sources (and/or sources of other radiation) that project light to the rotatable optical fiber via the first optical fiber and the optical connection between the first optical fiber and the rotatable optical fiber.

At 910, process 900 can include transmitting the optical signal from the static imaging device to the rotatable optics of the probe via the optical connection between the first optical fiber and the rotatable optical fiber, and via the connection between the rotatable optical fiber and the rotatable optics.

At 912, process 900 can receive a return optical signal from the imaging probe that includes, for example, light that was reflected and/or emitted by a sample portion of the anatomy of a subject.

At 914, process 900 can include transmitting the optical signal from the rotatable optics of the probe to the static imaging device via the optical connection between the rotatable optical fiber and the rotatable optics, and via the connection between the first optical fiber and the rotatable optical fiber. Note that, in some embodiments, the optical signal from the imaging device and the optical signal from the probe can be transmitted simultaneously (e.g., by transmitting one signal using a core of the rotatable optical fiber, and transmitting another signal using an inner cladding of the rotatable optical fiber).

It will be appreciated by those skilled in the art that while the disclosed subject matter has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is hereby incorporated by reference, as if each such patent or publication were individually incorporated by reference herein.

Various features and advantages of the invention are set forth in the following claims.

What is claimed is:

1. A lens-less optical rotary joint, comprising:
   a guide ferrule;
   a rotatable ferrule;
   a rotatable optical fiber,
      the rotatable optical fiber passing through the rotatable ferrule and the guide ferrule,
      the rotatable optical fiber being secured within the rotatable ferrule, and
      the rotatable optical fiber being freely rotatable within the guide ferrule; and
   a coupler to secure the guide ferrule and receive a static ferrule including a static optical fiber such that a face of the static optical fiber is proximate a face of the rotatable optical fiber.

2. The lens-less optical rotary joint of claim 1, further comprising a gap between the face of the static optical fiber and the face of the rotatable optical fiber.

3. The lens-less optical rotary joint of claim 2, wherein the gap between the face of the static optical fiber and the face of the rotatable optical fiber has a width of less than 50 µm.

4. The lens-less optical rotary joint of claim 2, wherein the guide ferrule comprises an end which mates with the static ferrule,
   wherein the end of the guide ferrule comprises a reference face which determines the width of the gap.

5. The lens-less optical rotary joint of claim 4, wherein the reference face has an area that is less than a cross-sectional area of the static ferrule.

6. The lens-less optical rotary joint of claim 1, wherein the rotatable optical fiber is a multi-mode optical fiber, and
   wherein the lens-less optical rotary joint is compatible with multi-mode optical fibers and single mode optical fibers.

7. The lens-less optical rotary joint of claim 1, further comprising a rotatable shaft at least partially enclosing the rotatable ferrule such that rotation of the rotatable shaft around a central axis defined by the rotatable optical fiber causes rotation of the rotatable ferrule around the central axis.

8. The lens-less optical rotary joint of claim 1, further comprising:
   an optical coherence tomography probe comprising rotatable optics,
      wherein the optical coherence tomography probe is coupled to the rotatable optical fiber; and
   a static imaging device,
      wherein the static imaging device is coupled to the static optical fiber,
         wherein a plurality of continuous optical connections are formed between the static imaging device and the optical coherence tomography probe during rotation of the rotatable optics.

9. The lens-less optical rotary joint of claim 1, wherein the rotatable ferrule and the guide ferrule are separated by a spacing.

10. The lens-less optical rotary joint of claim 2, wherein the gap has a transmission fluid disposed therein.

11. The lens-less optical rotary joint of claim 10, wherein the transmission fluid comprises an index matching gel.

12. A method for transmitting optical signals from a static imaging device to an imaging probe with rotatable optics using a lens-less optical rotary joint, wherein the lens-less optical rotary joint comprises:
   a guide ferrule;
   a rotatable ferrule;
   a rotatable optical fiber that passes through the rotatable ferrule and the guide ferrule, wherein the rotatable optical fiber is secured within the rotatable ferrule and is free to rotate within the guide ferrule; and
   a sleeve that is configured to secure the guide ferrule and receive a static ferrule including a static optical fiber such that a face of the static optical fiber is brought into close proximity to a face of the rotatable optical fiber;
   wherein the method comprises:
   connecting the static optical fiber to the lens-less optical rotary joint by inserting the static ferrule into the sleeve to form a first connection;
   connecting the rotatable optics of the imaging probe to the rotatable optical fiber by coupling the rotatable optics into a rotatable optical connector to form a second connection;
   rotating the rotatable optical fiber and the rotatable optics;
   receiving a first signal from the static imaging device;
   transmitting the first signal to the rotatable optics through the first connection and the second connection during rotation of the rotatable optical fiber; and
   receiving a second signal from the imaging probe; and
   transmitting, simultaneously with transmission of the first signal, the second signal to the static imaging device through the first connection and the second connection during rotation of the rotatable optical fiber.

13. The method of claim 12, wherein the lens-less optical rotary joint further comprises a gap between the rotatable optical fiber and the static optical fiber.

14. The method of claim 13, wherein the gap has an index matching gel disposed therein.

15. The method of claim 13, wherein the gap has a width of less than 50 µm.

16. The method of claim 12, wherein the guide ferrule and the rotatable ferrule are separated by a spacing.

* * * * *